United States Patent [19]
Cuffe

[11] Patent Number: 6,016,700
[45] Date of Patent: Jan. 25, 2000

[54] SIGNAL PROCESSING APPARATUS FOR ULTRASONIC FLAW DETECTION SYSTEM

[75] Inventor: John M. Cuffe, State College, Pa.

[73] Assignee: Krautkramer Branson, Inc., Lewistown, Pa.

[21] Appl. No.: 08/959,677

[22] Filed: Oct. 29, 1997

[51] Int. Cl.[7] .................................................. G01N 29/00
[52] U.S. Cl. ................................ 73/602; 73/596; 702/39
[58] Field of Search ............................ 73/596, 597, 598, 73/599, 600, 602, 609, 610; 702/33, 35, 39

[56]  References Cited

U.S. PATENT DOCUMENTS

| | | | |
|---|---|---|---|
| 4,858,469 | 8/1989 | Hosgood et al. | 73/579 |
| 5,269,309 | 12/1993 | Fort et al. | 128/661.01 |
| 5,287,291 | 2/1994 | Cuffe et al. | 702/39 |
| 5,513,531 | 5/1996 | Sapia et al. | 73/602 |
| 5,569,853 | 10/1996 | Mignot | 73/602 |
| 5,671,154 | 9/1997 | Iizuka et al. | 702/39 |
| 5,907,098 | 5/1999 | Tsuboi et al. | 73/579 |
| 5,907,100 | 5/1999 | Cook | 73/602 |
| 5,911,160 | 6/1999 | Abe et al. | 73/602 |

Primary Examiner—Richard A. Moller
Attorney, Agent, or Firm—Polster, Lieder, Woodruff & Lucchesi

[57] ABSTRACT

Apparatus (10) for processing a return waveform generated by directing an ultrasonic pulse at an object (S) under test. A signal converter (12) converts the return waveform from an analog to a digital signal. The analog-to-digital conversion rate is approximately four times the operating frequency of the ultrasonic pulse. A signal processor includes a plurality of digital signal processors (14,16,18) each of which is separately controllable to process the converted digital signal. A communications network (20) directs the analog signal, converted digital signal, and an output signal from the signal processor to a visual display (28) and to various peripheral equipment (A1,A2) connected to the apparatus. A process controller (22) controls routing of these signals to and from the signal processor over the communication network. By processing a return waveform, peak amplitude values representing flaws or imperfections in the object can be determined and the processed waveform, including peak values, displayed.

30 Claims, 3 Drawing Sheets

SIGNAL PROCESSING APPARATUS FOR ULTRASONIC FLAW DETECTION SYSTEM

CROSS-REFERENCE TO RELATED APPLICATIONS

None.

STATEMENT REGARDING FEDERALLY SPONSORED RESEARCH OR DEVELOPMENT

Not Applicable.

BACKGROUND OF THE INVENTION

This invention relates to the ultrasonic, non-destructive testing of objects, and more particularly to apparatus employing digital signal processing and digital signal processing techniques for processing and displaying the results of such tests.

In copending U.S. Pat. No. 5,596,508, issued Jan. 21, 1997 entitled, "High Resolution Measurement of a Thickness Using Ultrasound," there is described an apparatus and a method for making highly accurate measurements of a material thickness using ultrasound. This non-destructive testing technique involves propagating an ultrasonic waveform having defined characteristics at an object or test specimen, and evaluating a return waveform to determine the attributes of the object or specimen to the desired degree of accuracy. In performing ultrasonic testing to measure material thickness, it is known to use sampling rates on the order of 100–500 MHz to obtain an accuracy level of $10*10^{-6}$ inches, and it is not unknown to use sampling rates in the gigahertz range. The electronic circuits typically used in processing test data to acquire these numbers for samples is emitter-coupled logic, or ECL. Further, it has heretofore been common to employ analog signal processing to generate a visual display of the return waveform which is then evaluated by an operator to determine whether or not the test specimen meets required specifications.

As an alternative to conventional ultrasonic testers, it is now possible to employ digital signal processing to evaluate the response waveforms and to perform pass/fail evaluations. A major advantage of using digital signal processing is that the sampling rate can now be on the order of 50 MHz, and still provide highly accurate measurement information to the user. Further, employing digital signal processing techniques enhances the accuracy of the results. In addition, digital signal processing techniques allow the signal processor to be interfaced with existing test equipment such as that described in the copending application, as well as other types of test equipment. Further, the signal processor apparatus can now provide a waveform display and data storage features which enable the user to immediately ascertain if a test specimen is acceptable as well as perform post-test analysis of the data obtained.

BRIEF SUMMARY OF THE INVENTION

Among the several objects and features of the present invention may be noted the provision of an apparatus for use in the non-destructive testing of an object or test specimen;

the provision of such apparatus for processing an ultrasonic return waveform to obtain pertinent information about an object under test, and in particular the presence of flaws or imperfections which would make the object unsuitable for use;

the provision of such apparatus to process such waveform quickly and efficiently and to provide highly accurate test results from such processing, the results being visually displayed for viewing by test personnel, or supplied to peripheral equipment for further data processing and analysis;

the provision of such apparatus to employ a lower frequency ultrasonic pulse rate than other, conventional processors employ;

the provision of such apparatus to further employ digital signal processing and processing techniques which produce a desired level of accuracy which is at least comparable to results obtained using conventional test apparatus and signal processing techniques;

the provision of such apparatus to utilize curve fitting techniques as part of the waveform processing whereby amplitude peaks in the return waveform which represent areas of interest to be evaluated are readily and accurately ascertained to a desired level of resolution;

the provision of such apparatus to construct a waveform trace from processed data and present such a trace for observation by a user, the trace being generated using the curve fitting techniques employed by the apparatus;

the provision of such apparatus to further provide test data obtained from waveforn processing to an internal memory storage which is accessible by test personnel for subsequent processing and evaluation to determine acceptability of the object;

the provision of such apparatus to employ multiple signal processors for evaluation of return waveform data and to control their operation so as to quickly and efficiently process the data, ascertain waveform peaks, and provide an accurate visual representation, the waveforn processing required to determine acceptability of the specimen under test being independently performable by any of the signal processors or by a combination of processors;

the provision of such apparatus to employ a multi-channel capability so to be used in performing parallel testing of a number of specimens or multiple probe testing on a single specimen;

the provision of a method for signal processing anal for routing a variety of analog and digital signals within a processing apparatus so as to process waveforms and display the results of such processing, and to provide the results of the processing to the peripheral equipment;

the provision of such a method to be readily employed by test equipment and provide necessary signal processing by which the user can readily evaluate a return waveform and determine whether or not a material or object under test meets standards of acceptance;

the provision of such apparatus which is compatible with the apparatus described in copending U.S. patent application Ser. No. 08/350,956 to perform the return waveform processing required by the apparatus; and, the provision of such an apparatus and method to provides a relatively low cost, reliable, flexible, easy to use, and accurate signal processing capability for a user.

In accordance with the invention, generally stated, an apparatus is provided for processing a return waveform generated by directing an ultrasonic pulse at an object under test. A signal converter converts the return waveform from an analog to a digital signal at a conversion rate comparable to the frequency of the ultrasonic pulse. A signal processor includes a plurality of digital signal processors each of which is separately controllable to process the converted digital signal or which are usable in combination to perform the requisite processing. A communications network moves the analog signal, converted digital signal, and an output signal from the signal processor to a visual display and to various peripheral equipment connected to the apparatus. A controller of the apparatus routes these signals to and from the signal processor over the communications network. By processing a return waveform and displaying the results or providing the results to other equipment for analysis, peak amplitude values representing flaws or imperfections in the object can be determined and the processed waveform, including the peak values, displayed.

As a method, the invention includes converting the return waveform from an analog signal to a digital signal, this conversion being performed at a rate comparable to that of the frequency of the ultrasonic pulse. Next is processing the resulting digital signal by one of a plurality of digital signal processors each of which is separately controllable to process the digital signal or combining the operation of multiple processors to perform this task. Routing the analog signal, converted digital signal, and an output signal produced by the signal processing over a communications network enables the output signal to be directed to a visual display for displaying a reconstructed return waveform, and to peripheral equipment by which additional processing is performed. Finally, the method includes controlling the routing of the aforesaid signals to and from said signal processors over the communication network. Other objects and features will be in part apparent and in part pointed out hereinafter.

BRIEF DESCRIPTION OF THE SEVERAL VIEWS OF THE DRAWINGS

In the drawings.

Corresponding reference characters indicate corresponding parts throughout the drawings.

DETAILED DESCRIPTION OF THE INVENTION

Figure 1:
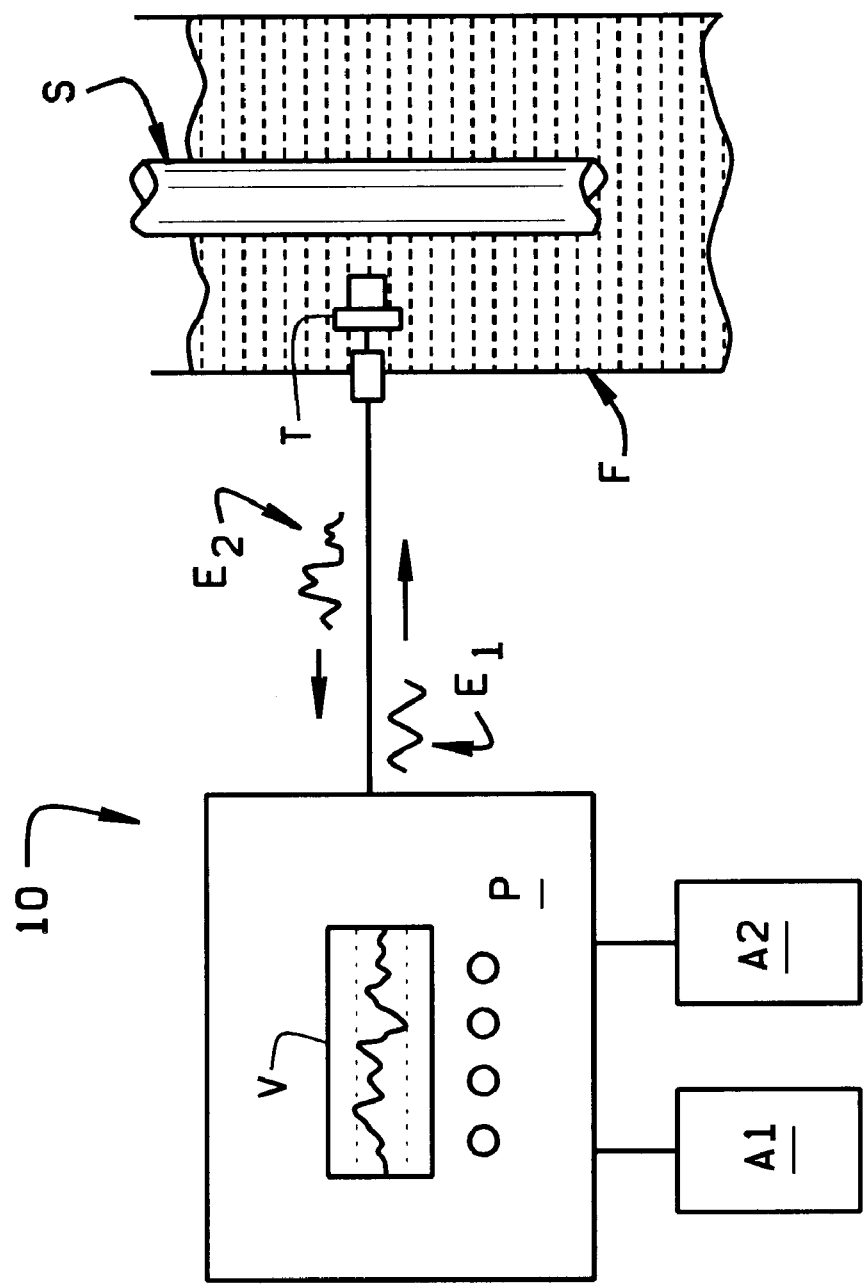
FIG. 1 is a simplified block diagram representation of an ultrasonic, non-destructive testing arrangement.

Referring to FIG. 1 of the drawings, an apparatus 10 of the present invention is for use in processing a return waveform produced by the generation and transmission of an ultrasonic waveform at an object under test. Reference is made to copending application Ser. No. 08/350,956, the teachings of which are incorporated herein by reference, with respect to the generation of an ultrasonic waveform directed at a tube or other test specimen. The tube, or any other test specimen (S) has certain characteristics such as wall thickness, for example, which must be determined to a high degree of accuracy. As indicated in the copending application, it is possible to measure this thickness to an accuracy of $10*10^{-6}$ inches.

As shown in FIG. 1, a test installation for ultrasonic, non-destructive testing of an object or test specimen (S) includes a test fixture (F), an ultrasonic transducer (T), and the signal processing apparatus 10 of the present invention. An electrical signal (E1) having defined waveform characteristics including a frequency is supplied to a transducer (T) from the signal processing apparatus 10. As is well-known in the art, the transducer converts the electrical signal to an ultrasonic pulse directed at the test specimen (S) and converts the ultrasonic pulse reflections from the test specimen (S) into an electrical return waveform (E2) relayed to the processing apparatus 10.

Figure 2:
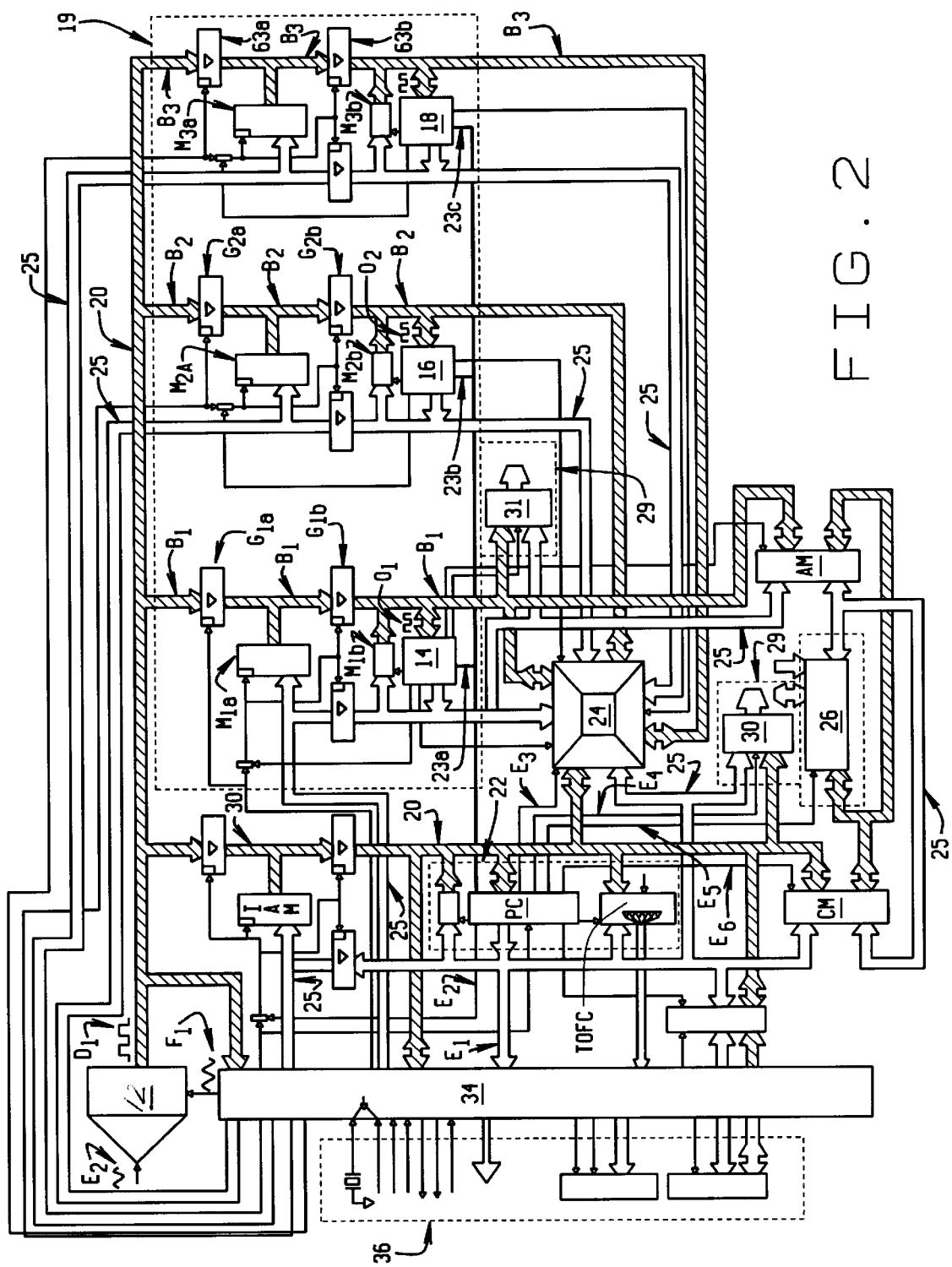
FIG. 2 is a schematic representation of the signal processing, routing, and control portion of the apparatus; and, FIG. 3 is representation of a control and display panel of the apparatus including an oscilloscope trace for displaying a processed, reconstructed return waveform.

Referring generally to FIG. 2, the electrical signal (E2) representing the return waveform is received by the signal processing apparatus 10 as one of two inputs to an analog-to-digital converter 12. The second input to the analog-to-digital converter 12 is a signal (F1) directly proportional to the rate at which test specimen (S) is subjected to ultrasonic pulses, approximately 50 MHz in the preferred embodiment, but as low as 10 MHz in alternate embodiments conforming to the teachings of copending application Ser. No. 08/350,956. The analog-to-digital converter 12 processes the two input signals to convert the return waveform signal to a digital signal representation (D1) of the original analog signal suitable for digital signal processing. The resulting digital signal (D1) is then routed from the output of the analog-to-digital converter 12 to three digital signal processors 14, 16, 18, of the signal processing unit 19 over a multi-channel data bus 20. Within the signal processing unit 19, the multi-channel data bus 20 has three branches, (B1, B2, B3) corresponding to each digital signal processor 14, 16, 18. The flow of digital data along branch (B1) is restricted by two unit-directional gates (G1a, G1b) whereby digital data on branch (B1) is only received by digital signal processor 14. In addition to routing the digital signal (D1), branch (B1) may route additional digital data from memory modules (M1a) and (M1b) to the digital signal processor 14 as needed. As is shown in FIG. 2, branches B2 and B3 are identical to branch B1, and have corresponding reference notations. In an alternate embodiment, the analog-to-digital converter 12 is multi-channel, capable of converting multiple signals simultaneously. Hence, the multi-channel data bus 20 is capable of transferring either a single digital signal (D1) or simultaneous separate digital signals (not shown) obtained from a plurality of test specimens (not shown) to each individual digital signal processor 14, 16, 18. In turn, each digital signal processor 14, 16, 18, is individually controlled by process controller 22 through enable lines 23a, 23b, 23c, to process all or a portion of each individual digital signal (D1) received from analog-to-digital converter 12. Processing of the digital signal (D1) or portions thereof may proceed in parallel or serial, as directed by the process controller 22. Process controller 22 contains a memory module (PCM), a processor unit (PC), and a signal time calculator (TOFC).

Digital signals received by the digital signal processors 14, 16, 18, are internally processed through pre-programmed curve-fitting algorithms and finite impulse response filters to derive digital data values representative of peak amplitude points for each ultrasonic return waveform. The peak amplitude points are representative of features of the test specimen S, such as flaws, cracks, or other discontinuities, and can be used to reconstruct the original analog return waveform (E2) for analysis and display. These digital data values representative of the peak amplitude points, are then provided as respective outputs (01, 02, 03) from the individual digital signal processors 14, 16, 18, as digital signals, and routed along the respective branches (B1, B2, B3) of the multi-channel data bus 20 to a data storage device 24.

Data storage device 24 is preferably comprised of a 4-port random access memory (RAM) module of sufficient size and speed to store the digital output signals (01, 02, 03). Access to the data contained within the data storage device 24 is controlled by the process controller 22. In addition to receiving the output digital signals (01, 02, 03) from each individual digital signal processor 14, 16, 18, data storage device 24 receives and stores the unprocessed digital signal (D1) produced by the analog-to-digital converter 12 by means of the multi-channel data bus 20. As is standard practice with random access memories, each storage location within the data storage device 24 is assigned a unique storage address. These addresses are communicated between the various components of the signal processing apparatus 10 by the branches and subsections of a multi-channel address bus 25 which is separate from the multi-channel data bus 20.

In addition to data storage device 24, the preferred embodiment of the claimed invention employs additional random access memory modules for data storage. These include a control RAM module (CM), a signal acquisition RAM module (AM), a peak segment RAM module (PSM), and an interface RAM module (IFM). Each of these memory modules is in data flow communication with the data bus 20 and the address bus 25, and is controlled for the storage and retrieval of digital data by the process controller 22.

Figure 3:
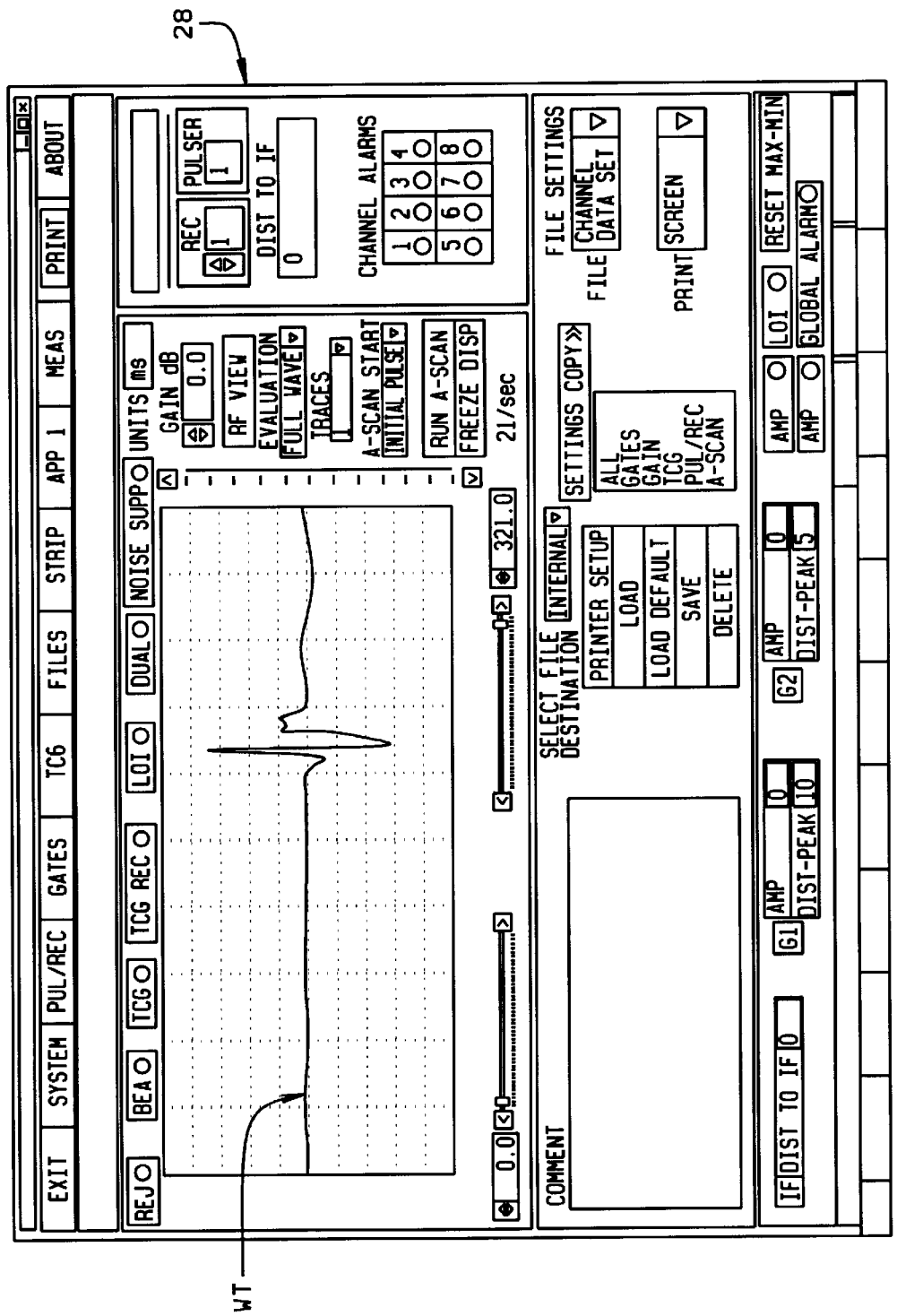

The processed digital data stored in data storage device 24 may be retrieved and routed by the process controller 22 over the multi-channel data bus 20 to a peripheral connection interface 26 for transfer to a display means 28 shown generally in FIG. 3, or to additional external devices (A1, A2) shown generally in FIG. 1 for additional data processing. The peripheral connection interface 26 is preferably a standard AT/PCI interface suitable for direct connection to the motherboard of a desktop computer system (not shown).

The preferred display means 28 shown generally in FIG. 3 employs a software algorithm capable of receiving the output digital signals (01, 02, 03) from the peripheral connection interface 26, and calculating a waveform trace (WT) representative of the original analog waveform (E2) received from said ultrasonic transducer (T). The operator may select from a variety of options when viewing waveform trace (WT) on the display means 28. These may include viewing the original radio-frequency signal, viewing a rectified signal half wave positive or negative, and viewing a rectified signal full wave. The various waveform traces are viewed without the use of specialized hardware to rectify the signals.

In addition to controlling the operation of the analog-to-digital converter 12, the digital 20 signal processors 14, 16, 18, and directing data flow over the data and address buses (20, 25), the process controller 22 regulates the operation of all input and output features of the signal processing apparatus 10 by means of enable lines (E1–E6). An output means 29 includes outputs 30 and 31 for an alarm signal and data validity signals. The alarm signal and the data validity signals are activated when the process controller 22 detects incoming data which exceed the operating parameters of the system. Data exceeding the operating parameters of the system is rejected by the process controller 22. Additional inputs and outputs to and from the process controller 22 such as timing signals and external analog controls shown generally at 36, are received and routed through a field programmable gate array interface circuit 34 to the various other components of the signal processing apparatus 10 over the multi-channel data and address buses 20, 25.

As a method, the ultrasonic signal processing of the claimed invention comprises the following preferred steps. First, the return analog waveform signals received from ultrasonic pulses are directed at one or more test specimens are received and routed to the signal converter for analog to digital conversion. Within the signal converter, the return analog waveform signals are processed along with a second set of input signals proportional to the frequency of the ultrasonic pulses directed at the test specimens to produce digital signals representative of the original analog return waveforms. The second set of input signals are within the range of 10 MHz to 50 MHz, and is in accordance with the teachings of copending application Ser. No. 08/350,956.

Next, the method includes routing the resulting digital signals a communications network consisting of multi-channel data buses to individually controlled digital signal processors. The digital signal processors process the received digital signals through preprogrammed curve-fitting algorithms to produce digital output signals representative of the original analog return waveforms peak amplitude values. The digital signal processors are controlled such that they may either process an individual waveform in parallel or may each independently process separate digital signals allowing for rapid analysis of multiple return signals. Upon completion of the digital signal processing, routing the digital output signals to appropriate data storage locations within a data storage means.

Further routing by the process controller may retrieve the digital output signals from the data storage means for transfer to either a display means or to an interface mean. Prior to display by the display means, the digital output data is reconstructed into waveform traces representative of the original analog return waveforms. Displayed as waveform traces, the digital output data enables an operator to quickly ascertain the characteristics and properties of the test specimen being examined. Similarly, digital output data routed by the process controller to the interface means may be processed or stored externally by external peripheral devices.

What has been described is a method and processing apparatus used in the ultrasonic testing of an object or test specimen for processing ultrasonic return waveforms reflected from a test specimen to obtain pertinent information about the specimen. It is a feature of the apparatus to process return waveforms quickly and efficiently, and to produce accurate test data as a result of the processing. A major advantage of the apparatus is the combination of a lower ultrasonic pulse rate than conventional processors employ and a lower sampling frequency, together with the use of curve-fitting techniques that allow the amplitude peaks in a return waveform to be readily ascertained at a desired level of resolution. The apparatus further can construct a waveform trace from the processed data and display the results for observation by a user. In addition, data derived from the waveform processing can be stored in an internal memory of the apparatus or directed to external equipment for subsequent processing and evaluation. The processing apparatus employs multiple signal processors for evaluating return waveforms and a process controller coordinates their operation for quick and efficient data processing. Each processor can process all or a portion of the return, and the processors can be used singly or in combination for this purpose. The apparatus has multi-channel capability and can be used for parallel testing of a plurality of specimens. Outputs from the processing are provided to display means and peripheral instrumentation for additional waveform analysis. The apparatus is compatible with existing ultrasonic testing apparatus and provides a signal processing capability by which a user can readily evaluate return waveforms to determine if a specimen meets standards of acceptance. Finally, the apparatus provides the user a greater degree of flexibility than existing equipment while still providing accurate results.

In view of the foregoing, it will be seen that the several objects of the invention are achieved and other advantageous results are obtained. As various changes could be made in the above constructions without departing from the scope of the invention, and it is intended that all matter contained in the above description or shown in the accompanying drawings shall be interpreted as illustrative and not in a limiting sense.

Having thus described the invention, what is claimed and desired to be secured by Letters Patent is:

1. Apparatus processing a return waveform from an ultrasonic pulse directed at a specimen under test to obtain information about the specimen comprising:

conversion means converting the return waveform from an analog signal to digital signal, a conversion rate at which said means for conversion performs a conversion being proportional to the frequency of the ultrasonic pulse;

processing means processing a converted waveform including a plurality of digital signal processors each of which is separately controllable to process the digital signal representing a converted waveform to produce an output signal containing return waveform data;

communication means directing said analog signal, digital signal, and output signal throughout the apparatus to provide return waveform data to a user of the apparatus; and, control means controlling routing of the aforesaid signals over said communication means.

2. The apparatus of claim 1 wherein said conversion means includes an analog-to-digital converter having as one input the return waveforms from said ultrasonic pulses, and as a second input a frequency signal proportional to the frequency of said ultrasonic pulses, said conversion means processing said first and second inputs to produce a digital signal representative of said return waveform.

3. The apparatus of claim 2 wherein the frequency of the second input signal to said analog-to-digital converter is approximately 50 MHz.

4. The apparatus of claim 2 wherein the frequency of the second input signal to said analog-to-digital converter is in the range of 10 MHz to 100 MHz.

5. The apparatus of claim 1 wherein said digital signal processors receive digital signals from said communication means and process said digital signals to obtain data representative of the specimen under test to determine if there are flaws, imperfections, or discontinuities in the specimen.

6. The apparatus of claim 5 wherein said digital signal processors process said digital signals through a curve-fitting algorithm using a finite impulse response filter to obtain data representative specimen under test.

7. The apparatus of claim 5 wherein the signal processing means includes three digital signal processors.

8. The apparatus of claim 5 wherein the control means includes means directing operation of each of said digital signal processors.

9. The apparatus of claim 5 wherein the control means includes means directing the operation of each of said digital signal processors, said means directing the operation of said digital signal processors in parallel such that each individual digital signal processor receives and processes a separate portion of the same digital signal.

10. The apparatus of claim 1 wherein said means for communication comprises a plurality of separate data buses and address buses to transport digital data.

11. The apparatus of claim 10 wherein said data buses are bidirectional data buses.

12. The apparatus of claim 10 wherein said data buses and address buses are multi-channel data buses allowing simultaneous transfer of multiple digital signals.

13. The apparatus of claim 10 further including a field programmable gate array interface having a plurality of input lines and a plurality of output lines, said field programmable gate array being in data flow communication with said data buses and address buses.

14. The apparatus of claim 13 further including second interface comprising a standard AT/PCI bus interface connector suitable for connection to, and communication with, external peripheral devices for the transfer of said analog, digital, and output signals to said external peripheral devices.

15. The apparatus of claim 14 further including display means in communication with said second interface and including means individually selecting, calculating, and displaying visual images representative of flaws, imperfections, or discontinuities a specimen under test.

16. The apparatus of claim 1 further including output means supplying an indication of digital signal values, and an indication of digital signal values exceeding valid range limitations.

17. The apparatus of claim 16 wherein the control means further includes means controlling the operation of the output means.

18. The apparatus of claim 1 further including data storing means in data flow communication with said communication means, said data storing means including means storing and retrieving in digital format, the digital signals from the conversion means.

19. The apparatus of claim 18 wherein the data storing means comprises a plurality of random access memory modules each capable of storing and retrieving digital data.

20. The apparatus of claim 19 wherein said control means includes controlling the operation of the data storing means including directing the storage of said digital and output signals received from said communication and retrieval of said digital signals and output signals for routing said signals over said communication means to said interface.

21. The apparatus of claim 1 wherein said control means comprises a plurality of control logic circuits connected to a plurality of control enable lines, said control enable lines routing control signals generated by said means for controlling to individual circuit elements to be controlled.

22. Apparatus processing analog return waveforms reflected from one or more specimens under test and at which ultrasonic pulses are directed to obtain information about the specimens, said apparatus comprising:

a converter converting each return waveform from an analog signal to a digital signal, the converter comprising an analog-to-digital converter having a rate of conversion proportional to the frequency of said ultrasonic pulses;

signal processing means including a plurality of digital signal processors each of which is separately controllable to process said digital signals received from the converter, each digital signal processor utilizing a curve-fitting algorithm to produce a digital output signal containing return waveform data representative of said specimens under test;

data storage means including random access memory modules digitally storing digital output signals from signal processing means and digital signals from said converter, said data storage means retrieving said stored signals;

an interface means for data access including connections for transferring digital signals between said apparatus and external peripheral equipment;

a display displaying waveform traces representative of said analog return waveform and of said data;

communication means including a plurality of multi-channel data buses each capable of simultaneously routing said digital signals and digital output signals throughout said apparatus; and, control means controlling the aforesaid routing of said digital signals over said communication means.

23. A method for digitally processing an analog return waveform from ultrasonic pulses directed at a specimen under test to obtain information about the specimen including the presence of flaws, imperfections, and discontinuities, the method comprising:

converting the analog return waveform to at least one digital signal, the conversion being performed at a rate comparable to the frequency of the ultrasonic pulses;

processing the resulting at least one digital signal by a signal processor to produce at least one digital output signal whose characteristic correspond to those of said analog return waveforn;

storing said at least one digital signal and said at least one digital output signal in a data storage means for subsequent retrieval;

routing said at least one digital signal and said at least one digital output signal over a communications means; and, controlling the operation of said signal processor, said data storage means, and the routing of the aforesaid signals over said communications means.

24. The method of claim 23 wherein said conversion of the analog return waveform to a digital signal is performed at approximately 50 MHz.

25. The method of claim 24 wherein said signal processor comprises a plurality of separately controllable digital signal processors, each digital signal processor utilizing a curve-fitting algorithm to process said at least one digital signal and produce said at least one digital output signal representative of said peak amplitude values from said at least one digital signal.

26. The method of claim 25 including separately controlling said digital signal processors such that only one of said digital signal processors processes said at least one digital signal and produces said at least one digital output signal.

27. The method of claim 25 including separately controlling said digital signal processors to simultaneously process separate portions of said at least one digital signal, each digital signal processor producing a plurality of digital output signals.

28. The method of claim 27 including separately controlling said digital signal processors to simultaneously process a plurality of separate digital signals simultaneously received for producing a plurality of digital output signals.

29. The method of claim 25 further including communicating over multi-channel data buses.

30. The method of claim 29 further including routing digital output signals to external peripheral equipment.

* * * * *

UNITED STATES PATENT AND TRADEMARK OFFICE
CERTIFICATE OF CORRECTION

PATENT NO : 6,016,700
DATED : January 25, 2000
INVENTOR(S) : John M. Cuffe

It is certified that error appears in the above-identified patent and that said Letters Patent is hereby corrected as shown below:

Col. 5, Line 46
Delete the number "20" between the words "digital" and "signal".

Signed and Sealed this

Twentieth Day of March, 2001

Attest:

NICHOLAS P. GODICI

Attesting Officer   Acting Director of the United States Patent and Trademark Office